United States Patent
Ferree

(10) Patent No.: US 6,685,695 B2
(45) Date of Patent: *Feb. 3, 2004

(54) METHOD AND APPARATUS FOR PROVIDING NUTRITION TO INTERVERTEBRAL DISC TISSUE

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 2 days.

This patent is subject to a terminal disclaimer.

(21) Appl. No.: 10/143,237

(22) Filed: May 10, 2002

(65) Prior Publication Data

US 2002/0128630 A1 Sep. 12, 2002

Related U.S. Application Data

(63) Continuation-in-part of application No. 09/688,716, filed on Oct. 16, 2000, now Pat. No. 6,454,804, and a continuation-in-part of application No. 09/639,309, filed on Aug. 14, 2000, now Pat. No. 6,419,702, which is a continuation-in-part of application No. 09/638,726, filed on Aug. 14, 2001, now Pat. No. 6,340,369.
(60) Provisional application No. 60/148,913, filed on Aug. 13, 1999.

(51) Int. Cl.[7] .................................................. A61F 2/44
(52) U.S. Cl. ....................................... 604/522; 623/908
(58) Field of Search ............................... 623/908, 17.11, 623/919, 923, 16.11; 434/93.7; 604/522

(56) References Cited

U.S. PATENT DOCUMENTS

| | | | |
|---|---|---|---|
| 6,340,369 B1 * | 1/2002 | Ferree | 623/17.11 |
| 6,402,784 B1 * | 6/2002 | Wardlaw | 623/17.11 |
| 6,419,702 B1 * | 7/2002 | Ferree | 623/17.11 |
| 6,443,988 B2 * | 9/2002 | Felt et al. | 623/17.12 |
| 6,454,804 B1 * | 9/2002 | Ferree | 623/17.11 |
| 6,554,830 B1 * | 4/2003 | Chappius | 606/61 |
| 6,564,078 B1 * | 5/2003 | Marino et al. | 600/373 |
| 6,572,654 B1 * | 6/2003 | Santilli | 623/17.16 |

OTHER PUBLICATIONS

Lumbar Intervertebral Disc Transfer a Canine Study, Steven Frick MD, Spine vol. 19 No. 16 pp. 1826–1835, 1994.
Orthopedics Today, Jul. 2000.
"Proceedings 14th Annual Meeting" North American Spine Society, Oct. 1999.
"Proceedings 13th annual Meeting" North American Spine Society, Oct. 1998.
North American Spine Society 13 Annual Meeting San Francisco Hilton and towers Oct. 28–31, 1998; Baron Lonner Md et al. Tissue Enineered Regeneration of the Intervertebral Disc.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

An intervertebral disc is treated by providing supplemental nutrition to increase viability and longevity. In the preferred embodiment, the invention uses one or more porous stents that function to irrigate the disc space. The stents provide channels for diffusion of fluids and nutrients from the vertebral endplates. The stents may extend across the vertebral endplates to facilitate the transfer of nutrients and oxygen from the vertebral bodies.

10 Claims, No Drawings

METHOD AND APPARATUS FOR PROVIDING NUTRITION TO INTERVERTEBRAL DISC TISSUE

REFERENCE TO RELATED APPLICATIONS

This application is a continuation-in-part of U.S. patent application Ser. No. 09/639,309, filed Aug. 14, 2000 now U.S. Pat. No. 6,419,702, which claims priority of U.S. Provisional Patent Application Serial No. 60/148,913, filed Aug. 13, 1999; and is a continuation-in-part of U.S. patent application Ser. No. 09/688,716, filed Oct. 16, 2000 now U.S. Pat. No. 6,454,804, which is a continuation-in-part of U.S. patent application Ser. No. 09/638,726, filed Aug. 14, 2000, now U.S. Pat. No. 6,340,369. The entire content of each application is incorporated herein by reference.

FIELD OF THE INVENTION

This invention relates generally to the treatment of intervertebral discs, and more particularly, to apparatus and methods for providing supplemental nutrition to intervertebral discs.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins. The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

The cells of the nucleus pulposus have chondrocyte-like features. In an adult human, the cells of the nucleus pulposis obtain nutrients and eliminate waste by diffusion through blood vessels in the endplates of the vertebrae adjacent to the disc. Blood vessels do not course into the nucleus pulposis. The relative vascular isolation of the nucleus pulposis imparts isolation of nucleus pulposis cells from the body's immune system.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wearout would be minimized, if not eliminated.

However, some researchers believe the vertebral endplates of vertebrae involved in degenerative disc disease do not allow sufficient diffusion of nutrition to the disc cells. Diseased endplates could thus lead to death of the intradiscal cells. Accordingly, any technique capable of providing or augmenting the delivery of such nutrition would be welcomed by patients and the medical community.

SUMMARY OF THE INVENTION

This invention is directed to a method of treating an intervertebral disc by providing supplemental nutrition to increase viability and longevity. In the preferred embodiment, the invention uses one or more porous stents that function to irrigate the disc space. The stents provide channels for diffusion of fluids and nutrients from the vertebral endplates. The stents may extend across the vertebral endplates to facilitate the transfer of nutrients and oxygen from the vertebral bodies.

DETAILED DESCRIPTION OF THE INVENTION

The invention resides in a methods and apparatus for providing nutrients to an intervertebral disc situated between the endplates of upper and lower vertebra. According to the method, a passageway is formed into the disc space. The process further includes the steps of placing a cannulated element in the passageway, and providing one or more substances beneficial to the intervertebral disc through the cannulated element. In the preferred embodiment, the cannulated elements take the form of porous stents which extend through the vertebral endplates.

The endplate stents according to the invention may be used to feed the disc cells within the disc naturally, and/or cells transplanted into the disc. In one application, transplanted disc tissue is placed around the disc stents at the time the disc tissue is added to the disc. Alternatively, the cells are grown in culture around the stents. In this way, the stents may support the growth of larger colonies of cells in cell culture. Given that colonies of cells grown in culture can reach a critical size where the cells in the center of the group can become deprived of nutrition, the stents would provide a channel for nutrients to the cells in the center of the colony.

In the embodiments involving the transplantation of biologic material in the form of nucleus pulposis cells or other tissues, live cells or tissues are harvested from a human or animal donor and introduced into the disc being treated. The harvested biologic materials are preferably kept viable until placed into the disc being treated. The harvested biologic materials may be introduced into the disc using any suitable transfer technique, including the formation of a passageway through the annulus fibrosis and the use of a needle and syringe or small cannula. Alternatively the step of transplanting may include percutaneously or laparoscopically injecting the cells or tissues into the disc being treated.

The invention may further include the use of an optional reservoir filled with therapeutic materials to aid the disc cells. For example, a refillable reservoir may be filled with cell-culture nutrients and placed in an accessible location under the skin of the flank. Other applicable therapeutic substances include, growth factors, differentiation factors, hydrogels, polymers, antibiotics, anti-inflammatory medications, or immunosuppressive medications.

If a transplanted nucleus pulposis is utilized, it is preferably harvested from a live human, though recently deceased human or animal donors may alternatively be used. Depending upon the extent of the harvest, the recipient may function at least in part as a donor, or the tissues from others, including fetal or embryo sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described in the literature.

Similarly, the guidelines for storage of living tissues are well known to those skilled in the art. The text "Organ Preservation for Transplantation" by Karow and Pego, 1981, describes such methods. Briefly, the tissue storage method must maintain cell viability and preserve sterility. Examples of present storage methods include: refrigeration, refrigeration with tissue culture medium such as: hemolyzed serum, autologous serum, Medium 199 with 5% dextran (McCarey-Kaufman medium), Medium 199 with chondroitin sulfate, Medium 199 supplemented with inorganic salts, short chain fatty acids, and/or ketone bodies, and cryopreservation techniques, among others. Details are provided in U.S. Pat. Nos. 4,695,536 and 4,873,186, the entire contents of which are incorporated herein by reference.

To minimize exposure to the recipient's immune system, the harvested nucleus pulposis is preferably inserted through a small hole in the annulus fibrosis using a blunttipped needle or cannula forced through the laminae. Upon withdraw of the needle, after injecting the transplanted nucleus pulposis, the separated fibers of the lamella return to their normal position, thereby sealing the annulus.

The annulus fibrosis is thicker in the anterior and lateral portion of the disc. Thus, the needle would preferably be inserted into the anterior or lateral portion of the disc. Those skilled in the art will realize the needle could be directed into the lateral portion of the disc percutaneously with fluourscopic guidance and into the anterior portion of the disc laparoscopically.

The host nucleus pulposis may be morselized to allow insertion into the disc through a small cannula or needle. The increased surface area of the nucleus pulposis after morsellization may also aid diffusion of nutrients and wastes products to and from transplanted disc cells. Alternatively large sections of the transplanted nucleus pulposis could be added to the disc if the annular defect was sealed after transplantation.

The transplanted nucleus is preferably added to the patient's nucleus pulposis. Alternatively, the patient's nucleus could be removed with standard techniques (enzymatically (chymopapain) or with the aid of a laser, suction device, shaver, or other surgical instrument). If the nucleus is removed the hole in the annulus should be small and sealed to prevent the ingrowth of vascular tissue. Vascular ingrowth could lead to a graft versus host reaction.

Additional therapeutic substances could be added to the transplanted nucleus. For example, resorbable culture medium, tissue growth or differentiation factors (recombinant generated morphogenetic proteins, PDGF, TGF-$\beta$, EGF/TGF-$\alpha$, IGF-I, $\beta$FGF), hydrogels, absorbable or nonresorbable synthetic or natural polymers (collagen, fibrin, polyglycolic acid, polylactic acid, polytetrafluoroethylene, etc.), antibiotics, antiinflammatory medication, immunosuppressive medications, etc. could be beneficial.

I claim:

1. A method of providing nutrients to an intervertebral disc situated between the endplates of upper and lower vertebra, comprising the steps of:

forming a passageway into the disc space;

placing a cannulated element in the passageway; and providing one or more substances beneficial to the intervertebral disc through the cannulated element.

2. The method of claim 1, wherein the passageway extends through one of the vertebral endplates.

3. The method of claim 1, wherein the beneficial substance contains a nutrient.

4. The method of claim 1, wherein the beneficial substance contains a therapeutic agent.

5. The method of claim 4, wherein the therapeutic agents include one or more of the following:

culture media, growth factors, differentiation factors, hydrogels, polymers, antibiotics, anti-inflammatory medications, or immunosuppressive medications.

6. The method of claim 1, further including the step of transplanting cells or tissues into the disc.

7. The method of claim 1, wherein the step of transplanting the cells or tissues includes the use a needle and syringe or small cannula through the annulus fibrosis.

8. The method of claim 1, wherein the step of transplanting the cells or tissues includes percutaneously or laparoscopically injecting the cells or tissues into the disc being treated.

9. The method of claim 1, further including the step of providing a reservoir containing the beneficial substance in communication with the cannulated element.

10. The method of claim 1, wherein the cannulated element is a stent.

* * * * *

UNITED STATES PATENT AND TRADEMARK OFFICE
CERTIFICATE OF CORRECTION

PATENT NO. : 6,685,695 B2
DATED : February 3, 2004
INVENTOR(S) : Bret A. Ferree

It is certified that error appears in the above-identified patent and that said Letters Patent is hereby corrected as shown below:

Title page,
Item [63], Related U.S. Application Data, replace "Aug. 14, 2001" with
-- Aug. 14, 2000 --.
Item [56], References Cited, U.S. PATENT DOCUMENTS, please insert the following:

| | | | |
|---|---|---|---|
| -- 2,677,369 | 05/04/1954 | Knowles | 128/92 |
| 3,366,975 | 02/06/1968 | Pangman | 3/36 |
| 3,426,364 | 02/11/1969 | Lumb | 3/1 |
| 3,551,560 | 12/29/1970 | Thiele | 424/95 |
| 3,593,342 | 07/20/1971 | Niebauer | 3/1 |
| 3,648,294 | 03/14/1972 | Shahrestani | 3/1 |
| 3,855,638 | 12/24/1974 | Pilliar | 3/1 |
| 3,867,728 | 02/25/1975 | Stubstad et al | 3/1 |
| 3,875,595 | 04/08/1975 | Froning | 3/1 |
| 3,883,902 | 05/20/1975 | Lynch | 3/36 |
| 4,229,839 | 10/28/1980 | Schwemmer | 1/1.91 |
| 4,309,777 | 01/12/1982 | Patil | 3/1.91 |
| 4,349,921 | 09/21/1982 | Kuntz | 3/1 |
| 4,663,358 | 05/05/1987 | Hyon et al | 521/64 |
| 4,707,872 | 11/24/1987 | Hessel | 5/451 |
| 4,714,469 | 12/22/1987 | Kenna | 623/17 |
| 4,759,766 | 07/26/1988 | Buettner-Janz et al | 623/17 |
| 4,772,287 | 09/20/1988 | Ray et al. | 623/17 |
| 4,801,299 | 01/31/1989 | Brendel et al | 633/16.11 |
| 4,863,477 | 09/05/1989 | Monson | 623/17 |
| 4,874,389 | 10/17/1989 | Downey | 623/17 |
| 4,904,260 | 02/27/1990 | Ray et al | 623/17 |
| 4,911,718 | 03/27/1990 | Lee et al | 623/17 |
| 4,917,704 | 04/17/1990 | Frey et al | 623/17 |
| 4,932,969 | 06/12/1990 | Frey et al | 623/17 |
| 4,946,378 | 08/07/1990 | Hirayama et al | 623/17 |
| 5,002,576 | 03/26/1991 | Fuhrman et al | 623/17 |
| 5,035,716 | 07/30/1991 | Downey | 623/17 |
| 5,047,055 | 09/10/1991 | Bao et al | 623/17 |
| 5,071,437 | 12/10/1991 | Steffee | 623/17 |
| 5,108,438 | 04/28/1992 | Stone | 623/17 |
| 5,123,926 | 06/23/1992 | Pisharodi | 623/17 |

UNITED STATES PATENT AND TRADEMARK OFFICE
CERTIFICATE OF CORRECTION

PATENT NO. : 6,685,695 B2
DATED : February 3, 2004
INVENTOR(S) : Bret A. Ferree

It is certified that error appears in the above-identified patent and that said Letters Patent is hereby corrected as shown below:

Title page (cont'd),

| | | | |
|---|---|---|---|
| 5,171,280 | 12/15/1992 | Baumgartner | 623/17 |
| 5,171,281 | 12/15/1992 | Parsons et al | 623/17 |
| 5,192,326 | 03/09/1993 | Bao et al | 623/17 |
| 5,246,458 | 09/21/1993 | Graham | 623/17 |
| 5,258,031 | 11/02/1993 | Salib et al | 623/17 |
| 5,258,043 | 11/02/1993 | Stone | 623/66 |
| 5,314,477 | 05/24/1994 | Marnay | 623/17 |
| 5,320,644 | 06/14/1994 | Baumgartner | 623/17 |
| 5,370,697 | 12/06/1994 | Baumgartner | 623/17 |
| 5,375,823 | 12/27/1994 | Navas | 267/195 |
| 5,401,269 | 03/28/1995 | Buettner-Janz et al | 623/17 |
| 5,425,773 | 06/20/1995 | Boyd et al | 623/17 |
| 5,458,642 | 10/17/1995 | Beer et al | 623/17 |
| 5,464,439 | 11/07/1995 | Gendler | 623/16.11 |
| 5,514,180 | 05/07/1996 | Heggeness et al | 623/17.11 |
| 5,534,028 | 07/09/1996 | Bao et al | 623/17 |
| 5,534,030 | 07/09/1996 | Navarro et al | 623/17 |
| 5,545,229 | 08/13/1996 | Parsons et al | 623/17 |
| 5,556,431 | 09/17/1996 | Buttner-Janz | 623/17 |
| 5,609,635 | 03/11/1997 | Michelson | 623/17 |
| 5,645,596 | 07/08/1997 | Kim et al | 623/17 |
| 5,645,597 | 07/08/1997 | Krapiva | 623/17 |
| 5,674,294 | 10/07/1997 | Bainville et al | 623/17 |
| 5,674,296 | 10/07/1997 | Bryan et al | 623/17 |
| 5,683,465 | 11/04/1997 | Shinn et al | 623/17 |
| 5,702,450 | 12/30/1997 | Bisserie | 623/17 |
| 5,711,960 | 01/27/1998 | Shikinami | 424/426 |
| 5,716,416 | 02/10/1998 | Lin | 623/17 |
| 5,800,549 | 09/01/1998 | Bao et al | 623/17 |
| 5,824,093 | 10/20/1998 | Ray et al | 623/17 |
| 5,824,094 | 10/20/1998 | Serhan et al | 623/17 |
| 5,865,845 | 02/02/1999 | Thalgott | 623/17 |
| 5,865,846 | 02/02/1999 | Bryan et al | 623/17 |
| 5,888,226 | 03/30/1999 | Rogozinski | 623/17 |
| 5,893,889 | 04/13/1999 | Harrington | 623/17 |
| 5,899,941 | 04/05/1999 | Nishijima et al | 623/17 |
| 5,928,284 | 07/27/1999 | Mehdizadh | 623/17 |
| 6,187,048 | 02/13/2001 | Milner et al | 623/17.12 |

UNITED STATES PATENT AND TRADEMARK OFFICE
CERTIFICATE OF CORRECTION

PATENT NO.    : 6,685,695 B2
DATED         : February 3, 2004
INVENTOR(S)   : Bret A. Ferree It is certified that error appears in the above-identified patent and that said Letters Patent is hereby corrected as shown below:

Title page (cont'd),

| | | | |
|---|---|---|---|
| 6,231,615 | 05/15/2001 | Preissman | 623/23.73 |
| 6,245,107 | 06/12/2001 | Ferree | 623/17.11 |
| 6,332,779 | 12/21/2001 | Boyce et al | 433/215 |
| 6,340,369 | 01/22/2002 | Ferree | 623/17.11 |
| 4,695,536 | 09/22/1987 | Lindstrom et al. | 435/1 |
| 4,873,186 | 10/10/1989 | Chen et al. | 435/1 |
| 6,060,053 | 05/09/2000 | Atala | 424/93.7 |
| 6,077,987 | 06/20/2000 | Breitbart et al. | 623/11.11 |
| 6,197,586 | 03/06/2001 | Bhatnager et al. | 435/395 |
| 6,352,557 | 03/05/2002 | Ferree | 623/17.11 |
| 6,419,702 | 07/16/2002 | Ferree | 623/17.11 |
| 6,454,804 | 09/24/2002 | Ferree | 623/17.11 -- |

Column 3,
Line 20, replace "blunttipped" with -- blunt-tipped --.

Signed and Sealed this

Twenty-sixth Day of October, 2004

JON W. DUDAS
*Director of the United States Patent and Trademark Office*